United States Patent [19]

Clow et al.

[11] 4,254,778
[45] Mar. 10, 1981

[54] IMAGING SYSTEMS

[75] Inventors: Hugh Clow, Maidenhead; Peter E. Walters, Southall; Wiliam S. Percival, West Ealing, all of England

[73] Assignee: EMI Limited, Hayes, England

[21] Appl. No.: 41,424

[22] Filed: May 22, 1979

[30] Foreign Application Priority Data

May 25, 1978 [GB] United Kingdom ............... 22291/78

[51] Int. Cl.³ .......................................... A61B 5/05
[52] U.S. Cl. ..................................... 128/653; 324/314
[58] Field of Search .................. 128/653; 324/307, 314

[56] References Cited

U.S. PATENT DOCUMENTS 3,789,832  2/1974  Domadian ............................ 128/653

OTHER PUBLICATIONS

Mansfield, P. "Proton Spin Imaging by Nuclear Magnetic Resonance", *Contemp. Physics*, 1976, vol. 17, No. 6, pp. 553–576.

Becker, E. D. et al., "Driven Equilibrium Fourier Transform Spectroscopy, A New Method for Nuclear Magnetic Resonance Signal Enhancement", *Jornl. of Amer. Chem. Soc.*, 91:27, Dec. 31, 1969 pp. 7784, 7785.

Easson, R. M., "Design & Performance of Yig-Tuned Gunn Oscillators," *Microwave Journal*, Feb. 1971, pp. 53–54, 56, 58, 68.

Hoult, D. I., "Zeugmatography; A Criticism of the Concept of a Selective Pulse in the Presence of a Field Gradient," Jrnl. of Mag. Res. 26, 165–167 (1977).

*Primary Examiner*—Robert W. Michell
*Assistant Examiner*—Francis J. Jaworski
*Attorney, Agent, or Firm*—Fleit & Jacobson

[57] ABSTRACT

In an apparatus for examining human bodies by nuclear magnetic resonance to produce images of cross-sectional slices of such bodies, it is desirable to reduce the recovery time between scans at different angles. A suitable pulse sequence for examination with minimum dispersion is disclosed. Repetition of the sequence with inverted pulses to drive the spins back to equilibrium and reduce recovery time is also disclosed.

9 Claims, 12 Drawing Figures

IMAGING SYSTEMS

The present invention relates to systems for providing images of distributions of a quantity, in a chosen region of a body, by gyromagnetic resonance, for example nuclear magnetic resonance (NMR) techniques. Such techniques may be used for examining bodies of different kinds. However a particularly beneficial application is the examination of patients for medical purposes.

Nuclear magnetic resonance is known for the analysis of materials, particularly by spectroscopy. Recently it has been suggested that the techniques be applied to medical examination to provide distributions of water content or relaxation time constants in sectional slices or volumes of patients. Such distributions are similar to, although of different significance from, the distributions of x-ray attenuation provided by computerised tomography (CT) systems.

Practical NMR systems operate by applying suitable combinations of magnetic fields to the body being examined, via coil systems, and detecting induced currents in one or more detector coil systems.

According to the invention there is provided a method of examining a body by nuclear magnetic resonance, including the steps of: applying to the body a steady magnetic field along an axis therein; applying a gradient field which, in conjunction with said steady field, gives a predetermined field in a slice of said body; in conjunction with the gradient field, applying a rotating magnetic field at the Larmor frequency for the field in the said slice to cause resonance therein; applying a second gradient field, 180° displaced in phase from the first and at a proportion of the magnitude thereof to reduce phase dispersion in said slice; applying a further magnetic field having a gradient across the slice in a chosen direction and sensing the resonance signal resulting from the slice during said further field, wherein, to reduce phase dispersion resulting from said fields, the first gradient field, rotating field, second gradient field and further field are repeated 180° displaced in phase.

In order that the invention may be clearly understood and readily carried into effect it will now be described by way of example with reference to the accompanying drawings, of which.

For the examination of a sample of biological tissue NMR primarily relates to protons, (hydrogen nuclei) in the tissue. In principle however, other nuclei could be analysed, for example, those of deuterium, tritium, fluorine or phosphorus.

Protons each have a nuclear magnetic moment and angular momentum (spin) about the magnetic axis. If then a steady magnetic field $H_{ZO}$ is applied to the sample the protons align themselves with the magnetic field, many being parallel thereto and some being antiparallel so that the resultant spin vector is parallel to the field axis. Application of an additional field $H_1$ which is an R.F. field of frequency related to $H_{zo}$, in a plane normal to $H_{zo}$, causes resonance at that frequency so that energy is absorbed in the sample. The resultant spin vectors of protons in the sample then rotate from the magnetic field axis (z-axis) towards a plane orthogonal thereto (x,y). The R.F. field is generally applied as a pulse and if $\int H_1 dt$ for that pulse is sufficient to rotate the resultant spin vectors through 90° into the x,y plane the pulse is termed a 90° pulse.

On removal of the $H_1$ field the equilibrium alignments re-establish themselves with a time constant $T_1$, the spin-lattice relaxation time. In addition a proportion of the absorbed energy is re-emitted as a signal which can be detected by suitable coils, at a resonant frequency. This resonance signal decays with a time constant $T_2$ and the emitted energy is a measure of the proton content of the sample.

As so far described, the resonance signal detected relates to the entire sample. If individual resonance signals can be determined for elemental samples in a slice or volume of a patient then a distribution of proton densities, in effect of water content, can be determined for that slice or volume. Additionally or alternatively it is possible to determine a distribution of $T_1$ or $T_2$.

In general the principles of analysing proton density by NMR in a slice of a body have been extensively discussed. The known techniques have been reviewed by P. Mansfield in Contemp. Phys. 17 (b) 1976, 553–576. Consequently the techniques will only be discussed in detail herein to the extent necessary to understand the improved arrangement of this invention.

In the embodiment discussed herein the examination is particularly of a cross-sectional slice of the patient, although examination of a larger volume is possible, either by examination of a plurality of adjacent slices, or by a specifically volume scan.

Figure 1:
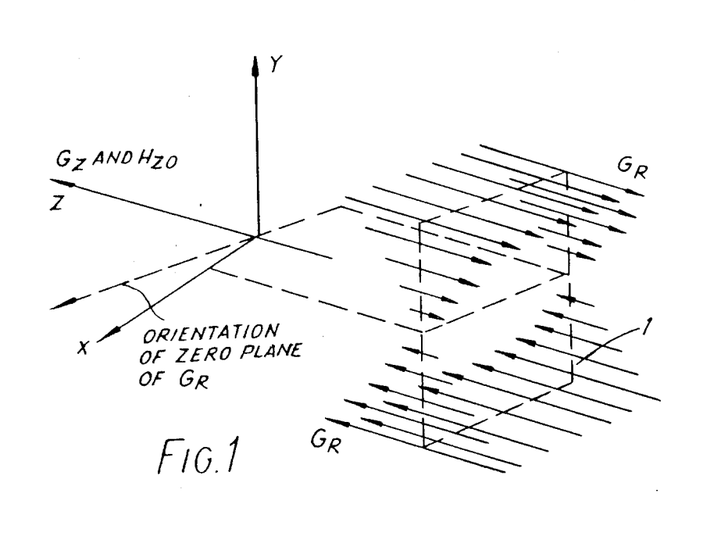
FIG. 1 shows the form of the $G_R$ field.
Figure 2:
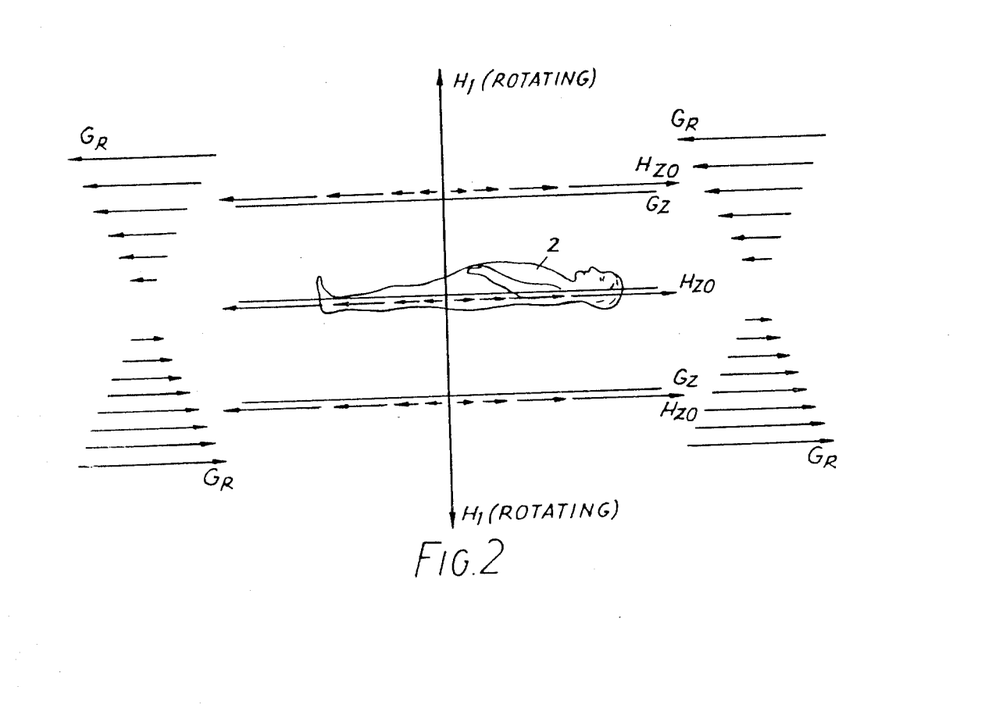
FIG. 2 shows the relationship of the $G_R$ field to the other field.

The first step is to ensure that resonance occurs at the chosen frequency only in the selected slice. Since the resonance frequency (the Larmor frequency) is related to the value of $H_{zo}$, the slice selection is achieved by imposing a gradient on $H_{zo}$ so that the steady field is of different magnitude in different slices of the patient. The steady and uniform $H_{zo}$ field is applied as before, usually longitudinal to the patient. An additional magnetic field $G_z$ is also applied, being a gradient $G_z = \partial H_z/\partial z$. If then the pulsed $H_1$ field is applied at the appropriate frequency, resonance only occurs in that slice in which the resonance frequency as set by $H_{zo}$ and the local value of $G_z$ is equal to the frequency of $H_1$. If the $H_1$ pulse is a 90° pulse, it brings the spin vectors into the x, y plane only for the resonant slice. Since the value of the field is only significant during the $H_1$ pulse, it is only necessary that $G_z$ be applied when $H_1$ is applied, and in practice $G_z$ is also pulsed. The $H_1$ and $G_z$ fields are therefore then removed. It is still, however, possible to change the resonant frequencies of the spin vectors which are now in the x, y, plane. This is achieved by applying a further field $G_R$, (actually $\partial H_z/\partial R$) which is parallel to $H_{zo}$. The intensity of $G_R$, however, varies from a maximum at one extreme of the slice, through zero in the centre to a maximum in the reverse direction on the opposite surface. The $G_R$ field is illustrated in FIG. 1, the arrows indicating only magnitudes at points on a rectangle 1. There will of course be a smooth variation through and between the magnitudes illustrated. The fields are also illustrated diagrammatically in the side elevation of FIG. 2 in relation to a patient 2. Correspondingly the resonant freqencies will vary smoothly over the plane of the slice from one side to the other.

As mentioned before, the signal which now occurs is at the resonant frequency. Consequently the signals received from the slice will also have frequencies which vary across the slice in the same manner. The amplitude at each frequency then represents inter alia the proton density in a corresponding strip parallel to the zero plane of $G_R$. The amplitude for each strip can be obtained by varying the detection frequency through the range which occurs across the slice. Preferably however the total signal at all frequencies is measured. This is then Fourier analysed by well known techniques to give a frequency spectrum. The frequency appropriate to each strip will be known from the field values used and the amplitude for each frequency is given by the spectrum.

As discussed, for the field $G_R$ illustrated in FIG. 1, the individual signals derived from the frequency spectrum, for increments of frequency, correspond to incremental strips parallel to the zero plane of $G_R$. These signals are similar in nature to the edge values derived and analysed for x-ray beams in computerised tomography. The X-ray edge values are obtained for sets at a plurality of different orientations in an examined slice and then are processed by a suitable method, such as that described in U.S. Pat. No. 3,778,614 and the further development thereof described in U.S. Pat. No. 3,924,129.

It will be apparent that by changing the orientation, relative to the x, y plane, of the zero plane of $G_R$, further sets of signals can be obtained representing proton densities along lines of further sets of parallel lines at corresponding further directions in the examined slice. The procedure is therefore repeated until sufficient sets of "edge values" have been derived to process by methods like those used for sets of x-ray beams. In practice the $G_R$ field is provided by combination of two fields $G_x$ and $G_y$, which are both parallel to $H_z$ but have gradients in orthogonal directions. The direction of the gradient of the resultant $G_R$ is therefore set by the relative magnitudes of $G_x$ and $G_y$. At many points in the following description reference will be made to the creation of $G_R$ field pulses and it should be remembered even where $G_x$ and $G_y$ fields are not individually discussed that reference is to the resultant of $G_x$ and $G_y$ field pulses.

Figure 3A:
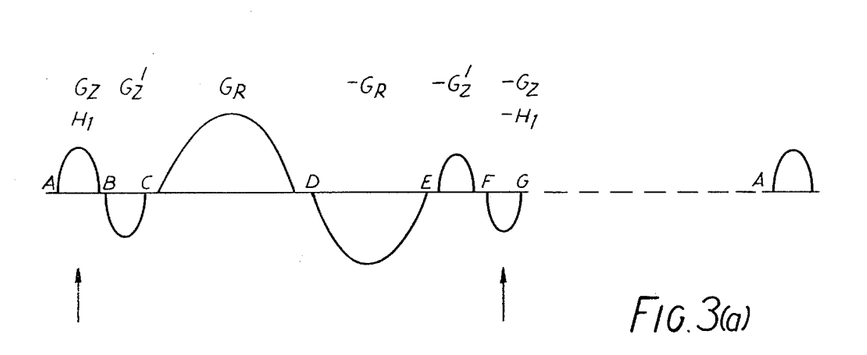
FIG. 3a shows the pulse sequence of this invention.
Figure 3B:
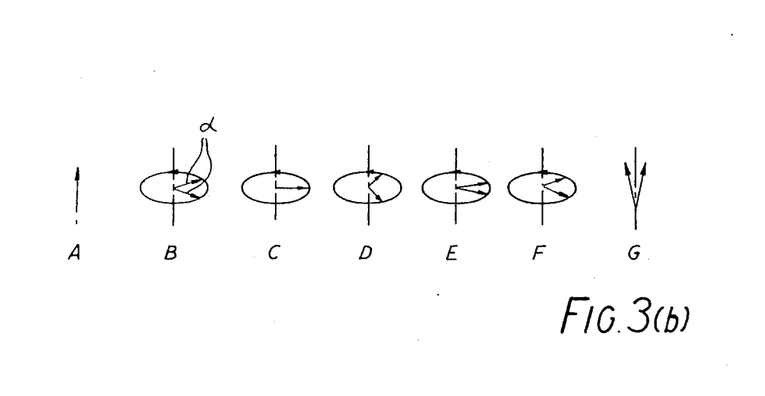
FIG. 3b shows the effects of the pulses of FIG. 3a on the proton spin vectors.

The full examination for one direction of the $G_R$ gradient is achieved by applying, via appropriate coils, the sequence of field pulses shown in FIG. 3a. FIG. 3b shows the effect which each pulse has on the spin vector. It will be appreciated that the $H_1$ field is a field rotating about the z-axis. Correspondingly the spin vectors thereafter precess about the z-axis. For clarity of explanation the spin vectors are shown in FIG. 3b on a coordinate system which rotates with $H_1$.

Referring to FIGS. 3a and 3b together, the pulse cycle comprises six phases, AB to FG, and a recovery period shown by the broken line. The $H_{zo}$ field is continuously present throughout the cycle.

Prior to the first pulse, or after the recovery period if an earlier cycle has been implemented, the mean spin moments are substantially aligned with the z-axis as shown at A in FIG. 3(b).

The gradient field $G_z$ pulse and $H_1$ pulses (AB), simultaneously applied, respectively select the slice and bring the resultant spin moments into the x, y plane (still, of course, precessing about the z-axis). Although the resonant frequency is the same throughout the slice selected, there is a phase dispersion introduced because the excitation occurred in a field gradient. Thus the spin moments are as shown at B in FIG. 3(b) though dispersed between limits much greater than can be satisfactorily illustrated. The limits shown at $\alpha$ are merely indicative of the nature of the dispersion. It has been found that this phase dispersion can be reversed by the application of a negative field gradient pulse, that is a pulse of the correct magnitude relative to $G_z$ but 180° displaced (the magnitude relation being about 55%). The use of such a 180° displaced pulse for rephasing has been proposed, see for example Hoult, J. Mag. Res. 26, 1977, 165. However the preferred magnitude relationship disclosed herein has not, it is believed, been previously disclosed. This pulse BC is therefore applied to bring the spin moments in the x, y plane into phase as shown in part C of FIG. 3(b). The $H_1$ field should not be continued into the negative gradient pulse ($G_z'$).

At that time a signal could be sensed to give proton density for the whole slice. However in this sequence, the signal is sensed in the presence of a $G_R$ pulse CD which gives frequency dispersion in a selected direction (r) in the slice as previously described. The change to the new frequencies is almost instantaneous with the application of the $G_R$ pulse and is maintained proportionately throughout the pulse. As discussed, the signal is sensed and frequency analysed to give the proton densities for a plurality of adjacent parallel strips of the slice. After the $G_R$ pulse, the spin moments, which are still largely in the x, y plane despite some relaxation, have a considerable phase dispersion as shown in part D of FIG. 3(b) (which is illustrative—as the actual dispersion is n $\pi$ (n being 100 or more)). At that stage, if a further cycle as described so far were to be required, it would be necessary to wait for spin-lattice relaxation to realign the spin movements with the z-axis. This could take as much as 5 seconds which, since hundreds, of or even several thousand cycles (i.e. several cycles for each of a hundred or more orientations of the zero plane of $G_R$) are required, is much too long.

It is proposed to return the spin moments substantially back to the starting position (part A of FIG. 3(b)) by repeating the pulse sequence up to D in the reverse order and reverse sense. Since the $-G_R$ pulse is substantially the same as the $G_R$ pulse except for its sense, further signals may be detected during it. These relate to the same r direction as for the forward pulse and help to improve the signal to noise ratio.

It will be realised that this procedure bears some relation to the so-called "DEFT" (Driven Equilibrium Fourier Transform) technique as disclosed for example by Becker et al. A. Amer. Chem. Soc. 91 (27) Dec. 31, 1969. 7784-5. DEFT is disclosed however only for spectroscopy systems and no disclosure is given of its relevance to body imaging. Consequently the disclosure only relates to reversal of the R.F. pulse sequence in the absence of gradient fields.

After the reverse pulse sequence, the spin moments still show some deviation from the z axis due to phase dispersions caused by spin-spin coupling. This cannot be reversed by this pulse sequence nor, it is believed, by any other. The period GA therefore allows some relaxation to thermal equilibrium (time constant $T_1$) which eliminates the effect of the phase dispersion and also reduces the effects of any mismatching between the forward and reverse pulses. Although the relaxation period GA is still necessary, the use of the reversed pulse sequence D to G much reduces that period and allows faster repetition of the total sequence for other r-directions. The length of the signal measurement period CE is influenced by the phase dispersion caused by $H_{zo}$ field inhomogeneity and also by the dispersion caused by spin-spin coupling. If the effect of $H_{zo}$ field inhomogeneity is considered to excessively shorten the period CE then pulse FG may be a 180° r.f. pulse rather than a 90° pulse. Turning the spin moments through 180° produces a so-called "spin-echo" of known form and the $G_R$ pulses similar to CD and DE can be repeated to give a further signal measurement period. The spin-echo procedure is known to reverse the dispersion due to field inhomogeneity and can be repeated here several times until sufficient signal has been obtained or until spin-spin dispersion, which cannot be reversed, becomes excessive. As in the sequence of FIG. 3(a), a spin-echo sequence should end with pulses EF, FG and recovery period GA.

In the case where a 90° $H_1$ pulse is used, the ratio of period GA to period AG should preferably be approximately the ratio of $T_1$ to $T_2$ for maximum sensitivity. An $H_1$ pulse less than 90° could be used as an alternative in which case the rates of the periods GA and AG should be appropriately reduced. Typically the total period AGA is 40 m sec where AG is approximately 5.5 m sec, AB is 300 μsec and CD is 2 m sec. The $H_1$ pulse is typically of 0.6 Oe and has a frequency of 4.26 MHz for an $H_{zo}$ of 1000 Oe. All other pulses are at envelope frequencies, $G_z$ being typically +30 Oe to −30 Oe, $G_R$ being 15 Oe to −15 Oe.

In the preferred embodiment $G_z'$ is less than $G_z$; typically $$\int G_z' dt = 0.55 \int G_z dt \text{ to } 0.60 \int G_z dt$$

As mentioned hereinbefore, the $G_R$ field pulses are the resultant of $G_x$ and $G_y$ components. The $G_x$ components are provided by four coils 3 and $G_y$ components by four coils 4, the coils 3 and 4 each comprising two pairs of saddle coils mounted on a common former as shown in FIG. 4; each pair being spaced from the other in the z-direction.

Figure 5A:
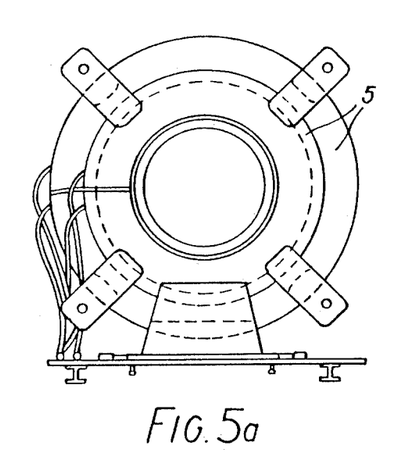
FIGS. 5a and 5b show the $H_{ZO}$ field coil of that machine.
Figure 5B:
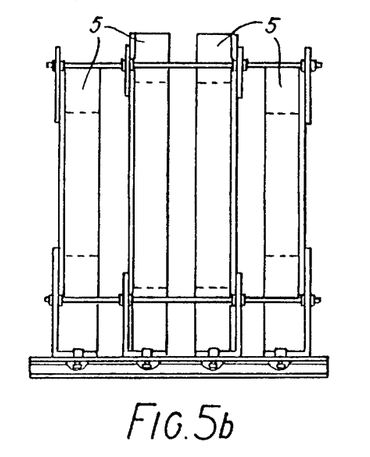

FIGS. 5a and 5b show in end and side elevation respectively a practical coil arrangement to provide the $H_{zo}$ field. The steady $H_{zo}$ field is provided by four coils 5 connected in series, although a smaller number could be used. Further details of the coil windings will not be given since suitable coils can readily be devised, by those with the appropriate skills, to provide the fields required.

Figure 4:
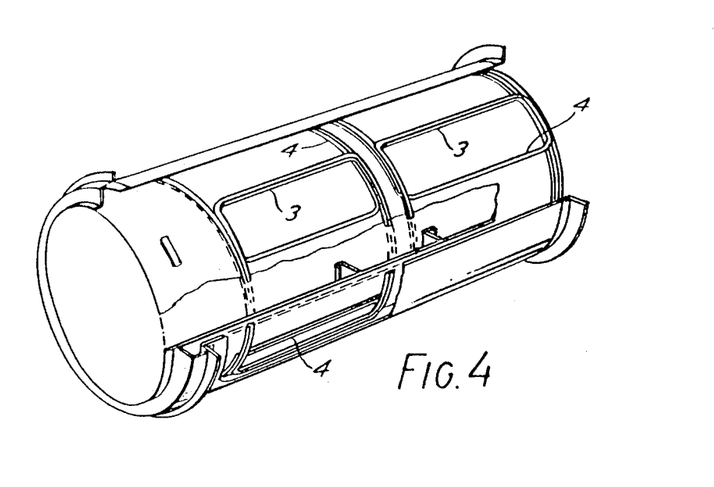
FIG. 4 shows typical $G_x$ and $G_y$ field coils in a practical NMR machine.

FIGS. 4, 5a and 5b do not show the $H_1$ and $G_Z$ coils so as to reduce the complexity of the drawings.

Figure 6:
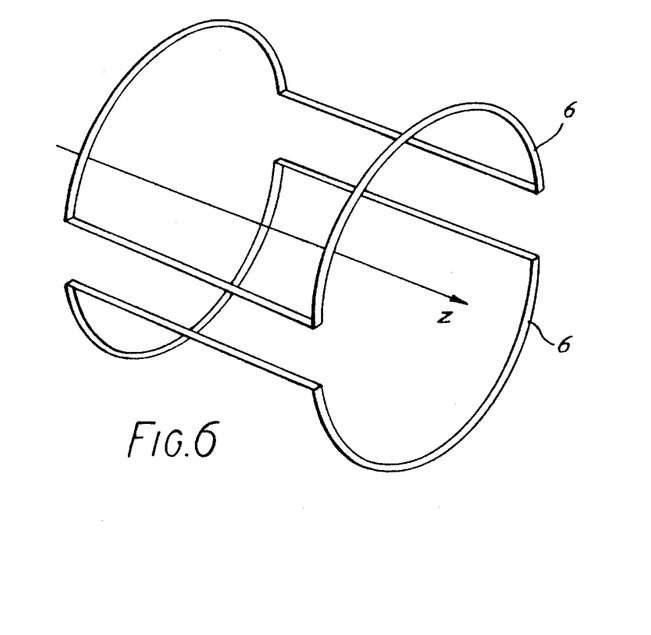
FIG. 6 shows the $H_1$ field coils of that machine.

The $H_1$ coils are shown in FIG. 6 in perspective. They comprise two saddle shaped coils 6 which are driven in parallel to provide the $H_1$ field and which are, in this example, also used to detect the signals which are of approximately the same frequency. It can be advantageous to use separate receiving coils, however, for signal detection.

Figure 7:
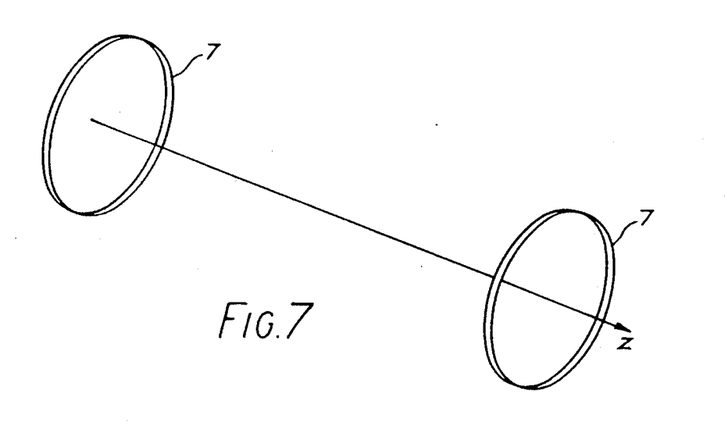
FIG. 7 shows the $G_z$ field coils of that machine.

FIG. 7 shows, also in perspective, two circular coils 7 which provide the $G_z$ field component for the gradient superimposed on $H_{zo}$.

Also included in the coil system are a set of field measurement probes whose purpose will be discussed further hereinafter. Four of these are yttrium iron garnet tuned oscillators (so called "YIG oscillators") and there is also at least one simple NMR probe.

The NMR apparatus described so far can be constructed by those with experience in this art to provide the required data for a slice of a patient's body. For sufficiently accurate results to give diagnostically useful information it is, however, desirable, and in some cases important, that some factors, in particular the magnetic fields, are precisely controlled. For example it is desirable that the $H_{zo}$ field should be uniform to around 2 parts in $10^6$ over the examined slice. This uniformity can be affected by the quality of the coils used and by adjacent ferromagnetic materials, which should therefore be kept to a minimum.

Also requiring great precision are the $G_R$ gradient fields which, as discussed before, are constructed from $G_x (= G_R \sin \theta)$ and $G_y (= G_R \cos \theta)$ pulses. The $G_R$ gradient vector should be in the desired direction with the least error possible. Furthermore the $-G_R$ pulse should reproduce, in the opposite sense, the preceding $G_R$ pulse. Arrangements for the production of the required precision of the $G_R$ pulse are the subject of a U.S. patent application corresponding to British patent application No. 22295/78.

Figures 8, 9:
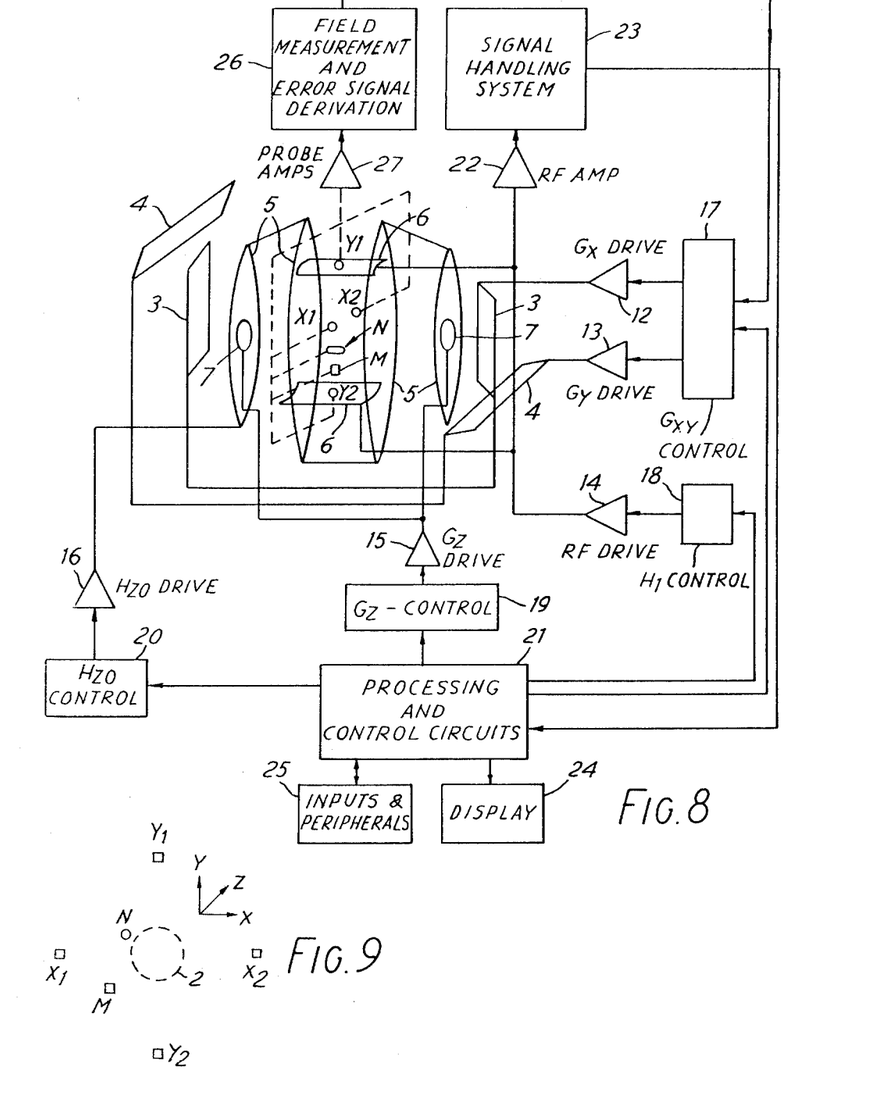
FIG. 8 shows a block diagram of the complete NMR apparatus.
FIG. 9 shows the disposition of the field sensing probes used.

FIG. 8 shows, in simplified form, an NMR apparatus, suitable for medical examination, employing the pulse sequence explained with reference to FIG. 3a and including field control for determination of the $G_R$ pulses.

The coils 3, 4, 5, 6 and 7, which are shown in highly schematic form, represent those shown hereinbefore, and identified by the same reference numbers, in FIGS. 4 to 7. They are driven by $G_x/G_y$, $R_F(H_1)$, $G_Z$ and $H_{ZO}$ control circuits, 17, 18, 19 and 20 respectively. These circuits can take suitable forms which will be known to those with experience of NMR equipment and other apparatus using coil induced magnetic fields. The circuits are controlled by circuits 21 to achieve the pulse sequence described or another appropriate one.

The signal to be sensed during the $G_R$ pulses is detected in the $H_1$ coils 6 and is amplified by a RF amplifier 22 before being applied to signal handling circuits 23. Circuits 23 are arranged to make any appropriate calibrations and corrections but essentially transmit the signals, which are effectively proton density values for lines in the body, to processing circuits to provide the required representation. These circuits can be specially designed to implement the CT type processing as described and claimed in U.S. Pat. No. 3,924,129. However it is advantageous to implement the processing by a suitably programmed digital computer. This computer can also conveniently control the pulse sequence and thus may also constitute the circuits indicated at 21. The picture thus obtained is viewed on a display 24, such as a television monitor, and this may include inputs and other peripherals 25 for the provision of commands and instructions to the machine or other forms of output.

Also included are field measurement and error signal circuits 26 which receive signals via amplifiers 27 from the field probes $X_1$, $X_2$, $Y_1$, $Y_2$, N and M shown. The positions of the probes, in relation to the examined slice of body 2, are further shown in FIG. 9. $X_1$, $X_2$, $Y_1$ and $Y_2$ are the YIG (yttrium-oxide-garnet) tuned oscillator probes referred to hereinbefore. These are standard magnetic field measuring probes such as described by R. M. Easson (The Microwave Journal, February 1971 pp. 53–58 and 68) or by Zublin et al (The Microwave Journal), September 1975 pp 33–35 and 50). These probes provide measures of the fields at the points at which they are situated as oscillations of field proportional to frequency (2.8 MHz/Oe). The values measured are therefore obtained by a count of the oscillations in a set time. In practice the YIG probes can oscillate in different modes and it is necessary to determine the mode in operation. For this purpose there are provided NMR probes M and N. Both of these probes are simply miniature cells of pure water (such as a closed test tube) surrounded by a small coil. They give a reliable resonance of 4.26 kHz/Oe and can be used to check the YIG tuned oscillator modes. They are, however, of insufficient spatial resolution to be used to replace the YIG probes for gradient field measurement. Probe N, fixed in space, acts as a reference, a moveable NMR probe M may be moved adjacent to the YIG modes in turn to provide data for determining their modes of oscillations, their orientation, and other performance observations. Once their calibrations are achieved, these probes in conjunction with NMR probe N can be used to generate the required signals for $G_R$ field control purposes.

Figure 10:
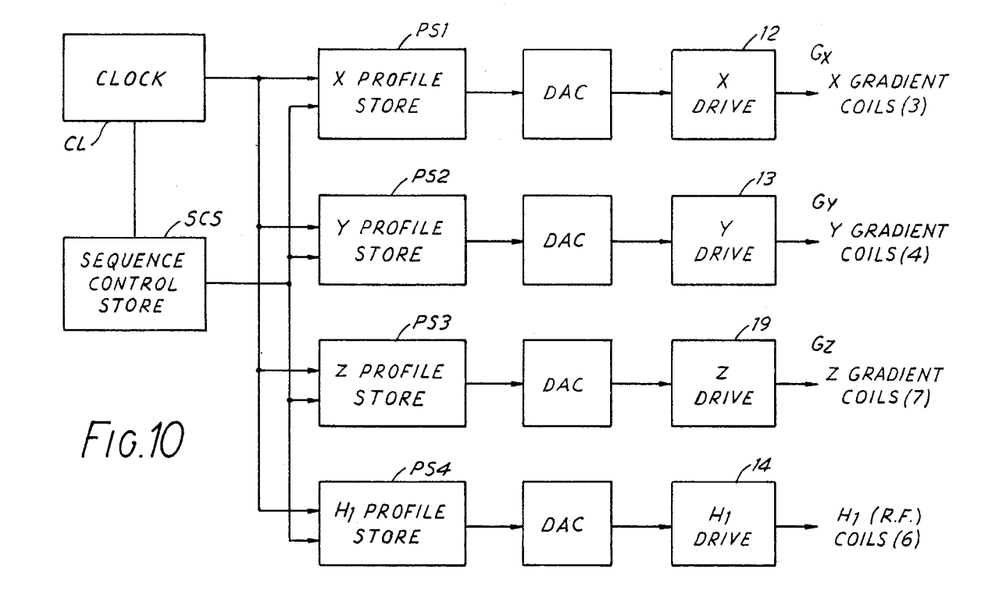
FIG. 10 shows typical processing and control circuits for use in the apparatus of FIG. 8.

FIG. 10 shows, in schematic view, components which may typically form part of the processing and control circuits of FIG. 10. Four profile stores PS1–4 store the required pulse shapes in terms of a sequence of current amplitudes and the required duration (number of clock pulses) at each amplitude. The specified current at any instant is then supplied by the corresponding drive circuit (12, 13, 19 or 14) to the corresponding coil (3, 4, 7 or 6). The operation of the four profile stores is controlled by a sequence control store SCS which stores the sequence of activation of the profile stores and the duration (number of clock pulses) of operation of each stage of the sequence (including gaps in the pulse sequence). A clock CL controls the overall timing operation of the circuits.

Considering the pulse sequence as described hereinbefore, it will be realised that there is a relatively long recovery period, GA, in which further information for the same slice cannot be obtained. This period can be used, however, to recover data for other slices. Although the time for one slice is long it will be clear that this interleaving allows examination of several slices in almost the same time. This data can be used to give an effective volume scan.

Typically the time required for any one slice examination is one eighth of the scan cycle. Thus eight slices can be examined in a single period only slightly longer than a single cycle. The effect is that one set of data for parallel lines in the slice is obtained for each slice in sequence. Then returning to the first slice, it is repeated for lines at a different angle and so on until all data for each slice is removed.

This NMR pulse sequence can be operated more efficiently if the Gx and Gy pulses are properly matched to each other and if the $G_R$ pulse is matched to the $-G_R$ pulse.

What we claim is:

1. A method of examining a body by nuclear magnetic resonance, including the steps of: applying to the body a steady magnetic field along an axis therein; applying a gradient field which, in conjunction with said steady field, gives a predetermined field in a slice of said body; in conjunction with the gradient field, applying a rotating magnetic field at the Larmor frequency for the field in the said slice to cause resonance therein; applying a second gradient field, 180° displaced in phase from the first and at a proportion of the magnitude thereof to reduce phase dispersion in said slice; applying a further magnetic field having a gradient across the slice in a chosen direction and sensing the resonance signal resulting from the slice during said further field, wherein, to reduce phase dispersion resulting from said fields, the first gradient field, rotating field, second gradient field and further field are repeated 180° displaced in phase.

2. A method according to claim 1 in which the resonance signal is also detected during the repetition of the further field.

3. A method according to either of claims 1 or 2 in which the resonance signal is also detected during the repetition of the further field.

4. A method according to claim 1 in which the second gradient field has a magnitude between 50% and 60% of that of the first gradient field.

5. A method according to claim 1 in which the repeated rotating field is sufficient to turn spin moments in the slice through 180° so that the further field and reversed further field can be repeated and the resonance signal further sensed during the second repetitions thereof.

6. A method according to claim 5 in which after the rotating field is repeated a plurality of times, in a form sufficient to turn the spin moments through 180° and followed each time by further and reversed further fields in which the resonance signal is sensed.

7. An apparatus for examining a body by nuclear magnetic resonance including means for applying to the body a steady magnetic field along an axis therein; means for applying a first gradient field, which, in conjunction with said steady field gives a predetermined field in a slice of said body, and a second gradient field 180° displaced from and at a proportion of the magnitude of said first gradient field; means for applying, at least in conjunction with the first gradient field, a rotating magnetic field at the Larmor frequency for the field in said slice to cause resonance therein; means for applying a further magnetic field having a gradient across the slice in a chosen direction; means for causing the means for applying said fields to repeat said fields but 180° displaced in phase; and means for sensing the resonance signal resulting from said slice at least during the first occurrence of said further field.

8. An apparatus according to claim 7 in which the means for causing said repetition is arranged to cause said fields to be repeated in reverse order.

9. An apparatus according to either of claims 7 or 8 in which the means for applying first gradient and rotating field are arranged to repeat these fields a plurality of times in which the rotating field is sufficient to turn the spin moments of bodies in the slice through 180° and repetitions are each followed by further fields and reversed further fields in which resonance signals are sensed.

* * * * *